United States Patent [19]

Bundy

[11] 4,156,782
[45] May 29, 1979

[54] 9-DEOXY-9-METHYLENE-13,14-DIDEHYDRO-16-PHENYL-PGF COMPOUNDS

[75] Inventor: Gordon L. Bundy, Portage, Mich.

[73] Assignee: The Upjohn Company, Kalamazoo, Mich.

[21] Appl. No.: 923,832

[22] Filed: Jul. 12, 1978

Related U.S. Application Data

[63] Continuation-in-part of Ser. No. 786,249, Apr. 11, 1977, Pat. No. 4,118,584.

[51] Int. Cl.² ............................................. C07C 177/00
[52] U.S. Cl. ........................................ 560/55; 560/60; 562/465; 562/470; 260/408; 260/410; 260/410.5; 260/413
[58] Field of Search ............................ 560/55; 510/60; 562/465, 470; 260/408, 410, 410.5, 413

Primary Examiner—Paul J. Killos
Attorney, Agent, or Firm—Robert A. Armitage

[57] ABSTRACT

The present invention relates to novel 9-deoxy-9-methylene-13,14-didehydro-16-phenyl-PGF compounds. These compounds are useful pharmacological agents, and are useful for the same purposes as the corresponding PGE-type compounds.

65 Claims, No Drawings

9-DEOXY-9-METHYLENE-13,14-DIDEHYDRO-16-PHENYL-PGF COMPOUNDS

CROSS REFERENCE TO RELATED APPLICATIONS

This application is a continuation-in-part of Ser. No. 786,249, filed Apr. 11, 1977, now issued as U.S. Pat. No. 4,118,584.

The present invention relates to a novel 9-deoxy-9-methylene-13,14-didehydro-16-phenyl-PGF-compounds, the essential material constituting a disclosure of which is incorporated here by reference from U.S. Pat. No. 4,118,584.

I claim:

1. A prostaglandin analog of the formula

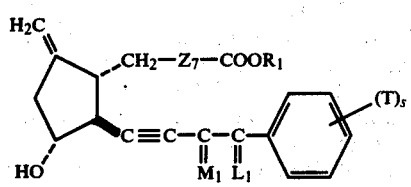

wherein $M_1$ is

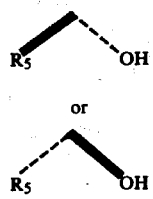

or

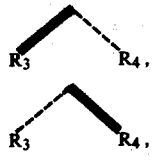

wherein $R_5$ is hydrogen or methyl; wherein $L_1$ is

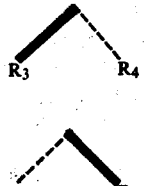

or a mixture of

and wherein $R_3$ and $R_4$ are hydrogen, methyl, or fluoro, being the same or different, with the proviso that one of $R_3$ and $R_4$ is fluoro only when the other is hydrogen or fluoro;

wherein $Z_7$ is
(1) cis-CH=CH—$CH_2$—$(CH_2)_g$—$CH_2$—,
(2) cis-CH=CH—$CH_2$—$(CH_2)_g$—$CF_2$—,
(3) cis-$CH_2$—CH=CH—$(C_2)_g$—$CH_2$—,
(4) —$(CH_2)_3$—$(CH_2)_g$—$CH_2$—, or
(5) —$(CH_2)_3$—$(CH_2)_g$-$CF_2$—, wherein
g is one, 2, or 3;
wherein T is chloro, fluoro, trifluoromethyl, alkyl of one to 3 carbon atoms, inclusive, or alkoxy of one to 3 carbon atoms, inclusive, and s is zero, one, 2, or 3, the various T(s being the same or different, with the proviso that not more than two T's are other than alkyl;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl or one to 3 carbon atoms, inclusive, or a pharmacologically acceptable cation, and the 1,11- or 1,15-lactones thereof.

2. A prostaglandin analog according to claim 1, wherein $Z_7$ is cis-$CH_2$—CH=CH—$(CH_2)_g$—$CH_2$—.

3. 9-Deoxy-9-methylene-cis-4,5-didehydro-16-phenyl-17,18,19,20-tetranor-13,14-didehydro-$PGF_1$, a prostaglandin analog according to claim 2.

4. A prostaglandin analog according to claim 1, wherein $Z_7$ is —$(CH_2)_3$—$(CH_2)_g$—$CH_2$—.

5. A prostaglandin analog according to claim 4, wherein $M_1$ is

6. 9-Deoxy-9-methylene-15-epi-16-phenyl-17,18,19,20-tetranor-13,14-didehydro-$PGF_1$, a prostaglandin analog according to claim 5.

7. A prostaglandin analog according to claim 4, wherein $M_1$ is

8. A prostaglandin analog according to claim 7, wherein s is zero or one and T is chloro, fluoro, or trifluoromethyl.

9. A prostaglandin analog according to claim 8, wherein g is 3.

10. 9-Deoxy-9-methylene-2a,2b-dihomo-15-methyl-16-phenyl-17,18,19,20-tetranor-13,14-didehydro-$PGF_1$, a prostaglandin analog according to claim 9.

11. 9-Deoxy-9-methylene-2a,2b-dihomo-16-phenyl-17,18,19,20-tetranor-13,14-didehydro-$PGF_1$, a prostaglandin analog according to claim 9.

12. A prostaglandin analog according to claim 8, wherein g is one.

13. A prostaglandin analog according to claim 12, wherein at least one of $R_3$ and $R_4$ is methyl.

14. A prostaglandin analog according to claim 13, wherein $R_3$ and $R_4$ are both methyl.

15. 9-Deoxy-9-methylene-16-methyl-16-phenyl-18,19,20-trinor-13,14-didehydro-$PGF_1$, a prostaglandin analog according to claim 14.

16. A prostaglandin analog according to claim 12, wherein at least one of $R_3$ and $R_4$ is fluoro.

17. A prostaglandin analog according to claim 16, wherein $R_3$ and $R_4$ are both fluoro.

18. 9-Deoxy-9-methylene-16,16-difluoro-16-phenyl-17,18,19,20-tetranor-13,14-didehydro-$PGF_1$, a prostaglandin analog according to claim 17.

19. A prostaglandin analog according to claim 12, wherein $R_3$ and $R_4$ are both hydrogen.

20. A prostaglandin analog according to claim 19, wherein $R_5$ is methyl.

21. 9-Deoxy-9-methylene-15-methyl-16-phenyl-17,18,19,20-tetranor-13,14-didehydro-$PGF_1$, a prostaglandin analog according to claim 20.

22. A prostaglandin analog according to claim 19, wherein $R_5$ is hydrogen.

23. 9-Deoxy-9-methylene-16-phenyl-17,18,19,20-tetranor-13,14-didehydro-PGF$_1$, a prostaglandin analog according to claim 22.

24. A prostacyclin analog according to claim 1, wherein Z$_7$ is cis-CH=CH—CH$_2$—(CH$_2$)$_g$—CH$_2$—.

25. A prostaglandin analog according to claim 24, wherein M$_1$ is

26. A prostaglandin analog according to claim 25, wherein s is zero or one and T is chloro, fluoro, or trifluoromethyl.

27. A prostaglandin analog according to claim 26, wherein g is 3.

28. 9-Deoxy-9-methylene-2$a$,2$b$-dihomo-15-epi-15-methyl-16-phenyl-17,18,19,20-tetranor-13,14-didehydro-PGF$_2$, a prostaglandin analog according to claim 27.

29. 9-Deoxy-9-methylene-2$a$,2$b$-dihomo-15-epi-16-phenyl-17,18,19,20-tetranor-13,14-didehydro-PGF$_2$, a prostaglandin analog according to claim 27.

30. A prostaglandin analog according to claim 26, wherein g is one.

31. A prostaglandin analog according to claim 30, wherein at least one of R$_3$ and R$_4$ is methyl.

32. 9-Deoxy-9-methylene-15-epi-16-methyl-16-phenyl-18,19,20-trinor-13,14-didehydro-PGF$_2$, a prostacyclin analog according to claim 31.

33. A prostaglandin analog according to claim 30, wherein at least one of R$_3$ and R$_4$ is fluoro.

34. 9-Deoxy-9-methylene-15-epi-16,16-difluoro-16-phenyl-17,18,19,20-tetranor-13,14-didehydro-PGF$_2$, a prostaglandin analog according to claim 33.

35. A prostaglandin analog according to claim 30, wherein R$_3$ and R$_4$ are both hydrogen.

36. 9-Deoxy-9-methylene-15-epi-15-methyl-16-phenyl-17,18,19,20-tetranor-13,14-didehydro-PGF$_2$, a prostaglandin analog according to claim 35.

37. A prostaglandin analog according to claim 24, wherein M$_1$ is

38. A prostaglandin analog according to claim 37, wherein s is zero or one and T is chloro, fluoro, or trifluoromethyl.

39. A prostaglandin analog according to claim 38, wherein g is 3.

40. A prostaglandin analog according to claim 39, wherein at least one of R$_3$ and R$_4$ is methyl.

41. 9-Deoxy-9-methylene-2$a$,2$b$-dihomo-16-methyl-16-phenyl-18,19,20-trinor-13,14-didehydro-PGF$_2$, a prostaglandin analog according to claim 40.

42. A prostaglandin analog according to claim 39, wherein at least one of R$_3$ and R$_4$ is fluoro.

43. 9-Deoxy-9-methylene-2$a$,2$b$-dihomo-16,16-difluoro-16-phenyl-17,18,19,20-tetranor-13,14-didehydro-PGF$_2$, a prostaglandin analog according to claim 42.

44. A prostaglandin according to claim 39, wherein R$_3$ and R$_4$ are both hydrogen.

45. 9-Deoxy-9-methylene-2$a$,2$b$-dihomo-16-phenyl-17,18,19,20-tetranor-13,14-didehydro-PGF$_2$, a prostaglandin analog according to claim 44.

46. A prostaglandin analog according to claim 38, wherein g is one.

47. A prostaglandin analog according to claim 46, wherein at least one of R$_3$ and R$_4$ is methyl.

48. A prostaglandin analog according to claim 47, wherein R$_3$ and R$_4$ are both methyl.

49. 9-Deoxy-9-methylene-16-methyl-16-phenyl-18,19,20-trinor-13,14-didehydro-PGF$_2$, tris(hydroxymethyl)aminomethane salt, a prostaglandin analog according to claim 48.

50. 9-Deoxy-9-methylene-16-methyl-16-phenyl-18,19,20-trinor-13,14-didehydro-PGF$_2$, methyl ester, a prostaglandin analog according to claim 48.

51. 9-Deoxy-9-methylene-16-methyl-16-phenyl-18,19,20-trinor-13,14-didehydro-PGF$_2$, a prostaglandin analog according to claim 48.

52. A prostaglandin analog according to claim 46, wherein at least one of R$_3$ and R$_4$ is fluoro.

53. A prostaglandin analog according to claim 52, wherein R$_3$ and R$_4$ are both fluoro.

54. A prostaglandin analog according to claim 53, wherein R$_5$ is methyl.

55. 9-Deoxy-9-methylene-15-methyl-16,16-difluoro-16-phenyl-17,18,19,20-tetranor-13,14-didehydro-PGF$_2$, a prostaglandin analog according to claim 54.

56. A prostaglandin analog according to claim 53, wherein R$_5$ is hydrogen.

57. 9-Deoxy-9-methylene-16,16-difluoro-16-phenyl-17,18,19,20-tetranor-13,14-didehydro-PGF$_2$, a prostaglandin analog according to claim 56.

58. A prostaglandin analog according to claim 46, wherein R$_3$ and R$_4$ are both hydrogen.

59. A prostaglandin analog according to claim 58, wherein R$_5$ is methyl.

60. 9-Deoxy-9-methylene-15-methyl-16-phenyl-17,18,19,20-tetranor-13,14-didehydro-PGF$_2$, tris(hydroxymethyl)aminomethane salt, a prostaglandin analog according to claim 59.

61. 9-Deoxy-9-methylene-15-methyl-16-phenyl-17,18,19,20-tetranor-13,14-didehydro-PGF$_2$, methyl ester, a prostaglandin analog according to claim 59.

62. 9-Deoxy-9-methylene-15-methyl-16-phenyl-17,18,19,20-tetranor-13,14didehydro-PGF$_2$, a prostaglandin analog according to claim 59.

63. A prostaglandin analog according to claim 58, wherein R$_5$ is hydrogen.

64. 9-Deoxy-9-methylene-16-phenyl-17,18,19,20-tetranor-13,14didehydro-PGF$_2$methyl ester, a prostaglandin analog according to claim 63.

65. 9-Deoxy-9-methylene-16-phenyl-17,18,19,20-tetranor-13,14-didehydro-PGF$_2$, a prostaglandin analog according to claim 63.

* * * * *